United States Patent [19]

Weaver et al.

[11] Patent Number: 4,896,047
[45] Date of Patent: Jan. 23, 1990

[54] METHOD AND APPARATUS OF PERIODICALLY OBTAINING ACCURATE OPACITY MONITOR READINGS OF AN EXHAUST GAS STREAM

[75] Inventors: Karen L. Weaver, Oviedo; James C. Bellows, Maitland, both of Fla.

[73] Assignee: Westinghouse Electric Corp., Pittsburgh, Pa.

[21] Appl. No.: 179,683

[22] Filed: Apr. 11, 1988

[51] Int. Cl.$^4$ ............................................. G01N 15/06
[52] U.S. Cl. ...................................... 250/573; 250/239
[58] Field of Search ............ 250/573, 574, 576, 231 R, 250/239; 350/582; 356/436, 437, 438, 440, 441, 442

[56] References Cited

U.S. PATENT DOCUMENTS

| | | | |
|---|---|---|---|
| 3,628,028 | 12/1971 | Thorsheim | 250/239 |
| 3,844,661 | 10/1974 | Birkett et al. | 350/582 |
| 3,861,198 | 1/1975 | Shea | 250/239 |
| 4,538,064 | 8/1985 | Kovacs | 250/231 R |
| 4,647,780 | 3/1987 | Dunkel | 250/573 |

Primary Examiner—David C. Nelms
Assistant Examiner—Khaled Shami
Attorney, Agent, or Firm—Michael G. Panian

[57] ABSTRACT

A method and apparatus for continually obtaining accurate opacity monitor readings of an exhaust gas stream (15) is disclosed. A conventional opacity monitor having a transmitter (10) and a receiver (13) is shielded from an exhaust stack (16) environment by two scratch-resistant windows (19, 20). The windows (19, 20) are periodically kept clean by spraying a volatile nonflammable cleaning solvent (28) onto each of the windows (19, 20), and a reciprocating resilient wiper arm (22) is used to remove the solvent (28) and any particulate matter (14) from the windows (19, 20). This cleaning is performed for a period of about twenty seconds. The next step is to then obtain an accurate opacity monitor by directing a light beam (34) across the stack (16) from the transmitter (10) via first window (19) through the exhaust gas stream (15) to the receiver (13) via second window (20). The reading is obtained during about the next ten seconds. By alternately repeating these steps, valid and accurate opacity monitor readings can be periodically obtained about every thirty seconds. Alternatively, a reciprocating brush (40) may be used part of the time to prevent accumulation of the particulate matter (14) on the windows (19, 20).

17 Claims, 2 Drawing Sheets

METHOD AND APPARATUS OF PERIODICALLY OBTAINING ACCURATE OPACITY MONITOR READINGS OF AN EXHAUST GAS STREAM

TECHNICAL FIELD

The invention relates to opacity monitors used to measure the degree of nontransparency of a gas stream and more particularly to a method and apparatus for periodically obtaining accurate opacity monitor readings of an exhaust gas stream.

BACKGROUND OF THE INVENTION

Opacity is a measurement of the degree of non-transparency of a gas stream. This measurement is required and regulated by most states for any industry which has any significant size exhaust stack emission to the atmosphere. A major group that is affected by this regulation, the purpose of which is to minimize the amount of particulate matter in the emissions, is the power industry. (This is based on BTU per hour and varies from state to state.) Most coal-fired and oil-fired power plants must monitor the amount of opacity in their stack emissions. However, current opacity monitors available require a great amount of maintenance to insure the acquisition of valid data. Current federal regulations require that opacity monitors produce valid data for 90% of the time. Many of the opacity monitors now in use require the full time attention of service personnel to achieve this level of data.

Opacity monitors work on the basis of a light beam which is directed horizontally across an exhaust stack or duct to a receiver on the opposite side. An example of such a monitor is described in U.S. Pat. No. 4,647,780 to Dunkel. The light beam continuously sent across is received by a lens and opacity is determined based upon a reading periodically taken. The receiver converts the intensity of the light beam received into an opacity reading based upon its difference from the known intensity of the transmitted beam. The more particulate matter present in the exhaust stream, the higher the opacity monitor reading. One of the problems with opacity meters is that the lens gets dirty with the accumulation of particulate matter from the exhaust gas stream and thus alters the opacity monitor reading. Traditionally the solution to this problem has been to have an instrument person manually wipe the lens clean at periodic times, usually several times per day. This approach has two drawbacks. First, an instrument person is needed to wipe the lens off. This may require calling him or her out in the middle of the night due to the fact that many power stations only work with a day shift instrument crew. Second, between cleanings the monitor may be giving falsely high readings. An alternate approach is to adjust the output of the opacity monitor in order to compensate for the build up of particulate matter on the lens. This approach still requires a person to manually wipe the lens off at some particular time. Air blowers across the lens, as in Dunkel, have been used but are ineffective in keeping the lens sufficiently clean over an extended period of time.

It is no minor task to perform the manual cleaning operation because of the location of the monitors, which are usually located on the stack as high as 91 m (300 feet). The time involved in such operations can be at least one hour to reach the monitors, clean the lens, and reassemble the monitor. As an additional concern, the monitor must be correctly calibrated so as to further provide for accurate readings. Due to vibrational effects the light beam may become misaligned and not fall directly on the receiver lens. Since it is a requirement that these monitors produce valid data 90% of the time, with readings obtained about once every 30 seconds, such operations can considerably reduce the available amount of time during which valid data can be obtained. Failure to satisfy these requirements and regulations could result in heavy fines being levied against the fossil fuel power plant operators.

It is therefore an object of the present invention to provide a method and apparatus for increasing the percentage of valid opacity monitor readings so as to reduce the possibility of having to pay regulatory fines.

It is another object of the present invention to provide a mechanical device to continually clean an opacity monitor which would not interfere with the acquisition of valid opacity monitor readings.

DISCLOSURE OF THE INVENTION

The above objects are obtained by the present invention, according to which, briefly stated, in an opacity monitor associated with an exhaust stack the monitor having a transmitter and a receiver which cooperate to measure the quantity of particulate matter in an exhaust gas stream, a method of periodically obtaining accurate opacity monitor readings is disclosed. The method comprises the steps of: shielding the monitor from the exhaust gas stream by placing two windows adjacent to the monitor, a first and second window being placed between the transmitter and receiver, respectively, and the exhaust gas stream. Each window is kept clean by spraying a volatile nonflammable cleaning solvent onto each of the windows by means of a sprayer intermittently operable during a first predetermined time period while being wiped by a reciprocating wiper arm in resilient engagement with the window, the wiper arm continually operable during the first predetermined time period. Then an accurate opacity monitor reading is obtained by directing a light beam across the exhaust stack from the transmitter through the exhaust gas stream to the receiver during a second predetermined time period. The steps of cleaning the windows during the first time period and then obtaining an accurate opacity monitor reading during the second time period are alternately repeated to periodically obtain accurate opacity monitor readings.

BRIEF DESCRIPTION OF THE DRAWINGS

The invention will become more apparent by reading the following detailed description in conjunction with the drawings, which are shown by way of example only, wherein.

DESCRIPTION OF THE PREFERRED EMBODIMENT

Figure 1:
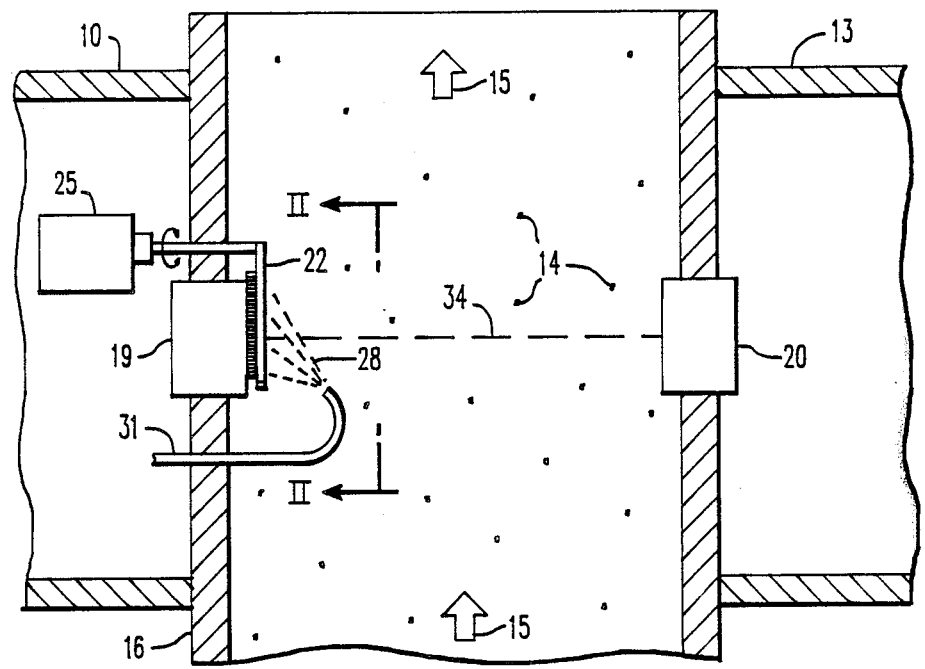
FIG. 1 is a cross-sectional, side-elevational view of an exhaust stack having an opacity monitor incorporating a continual cleaning method and apparatus according to the present invention.
Figure 2:
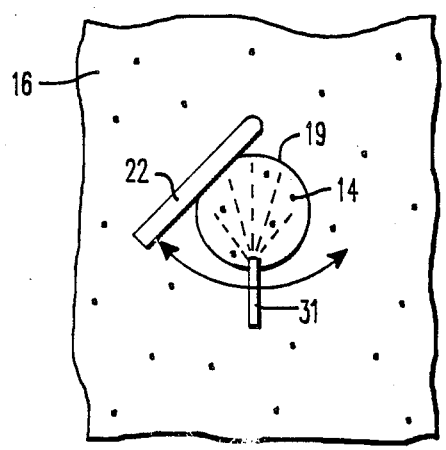
FIG. 2 is a view taken along the line II—II of FIG. 1.

Referring now to the drawings in detail, FIGS. 1 and 2 show a conventional opacity monitor having a transmitter 10 and a receiver 13 which cooperate to measure the quantity of particulate matter 14 in an exhaust gas stream generally designated by arrow 15. The monitor is shielded from the environment within the exhaust stack 16 by at least one, and preferably two windows or lenses 19, 20. In order to avoid the usual problem of erroneously high opacity monitor readings, at least one window is periodically wiped clean according to the present invention. A reciprocating resilient wiper 22, which is driven by a motor 25, continually wipes particulate matter 14 from the entire surface of the window 19 facing the exhaust gas stream 15 during a predetermined time period. The reciprocating resilient wiper 22, or other means for removing particulate matter 14 from the window 19, can be one similar to an automobile windshield wiper, or a brush-type device. To facilitate removal of particulate matter 14 from the window 19, a volatile nonflammable cleaning solvent 28 may be intermittently sprayed on the window 19 by a sprayer 31 during the predetermined time period. The cleaning solvent 28 is preferably 1,1,1 trichloroethane. This substance is desirable because it has no flash point, which is important since it is to be used in a high temperature zone. A similar cleaning substance that may be used is mineral spirits, or even water. As the wiper 22 moves across the window 19 it removes both the cleaning solvent 28 and any particulate matter 14 which may have accumulated on the window 19.

Figure 3:
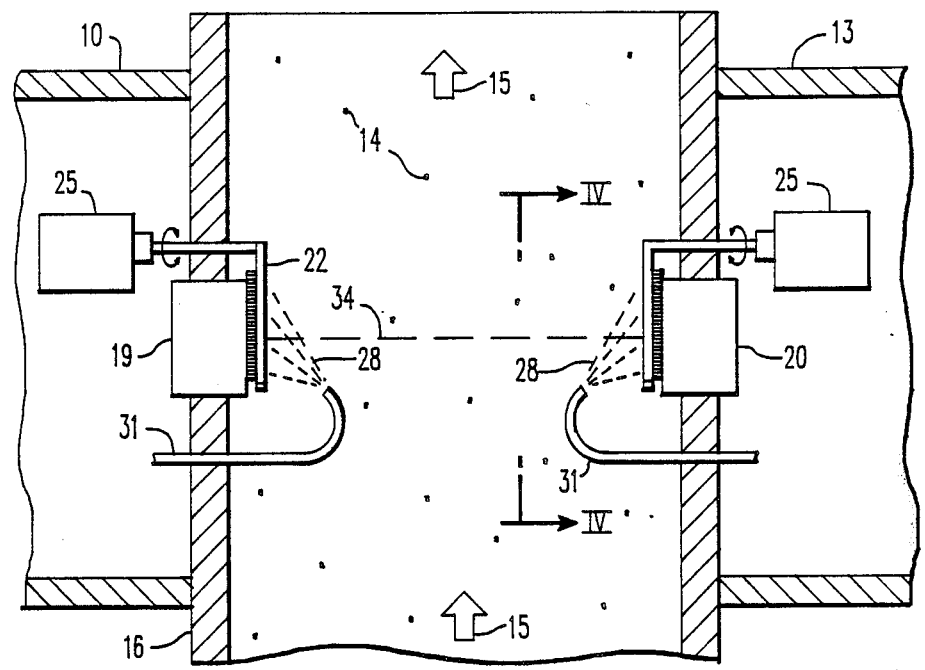
FIG. 3 is a cross-sectional, side-elevational view of an opacity monitor associated with an exhaust stack having both the transmitter and receiver shielded from the stack environment by an apparatus according to the present invention.

Although only one cleaning device is shown in place over the transmitter 10 of the monitor, it is understood that it may also be placed over the receiver 13. Most preferably, two such cleaning apparatuses are used to simultaneously clean both the transmitter 10 and the receiver 13 (FIG. 3). In this manner a light beam, represented by dashed line 34, sent across the stack 16 from the transmitter 10 to the receiver 13 encounters only particulate matter 14 that may be present in the exhaust gas stream 15; and not any particulate matter 14 which would otherwise accumulate on the windows 19, 20 and give rise to falsely high opacity monitor readings.

Since most state laws require an opacity monitor reading every thirty seconds, one method of periodically obtaining accurate opacity monitor readings from a monitor associated with an exhaust stack 16 would be as follows: The transmitter 10 and receiver 13 are shielded from the exhaust gas stream 15 by placing two windows 19, 20 adjacent to the monitor. A first window 19 is placed between the transmitter 10 and the exhaust gas stream 15, and a second window 20 is placed between the receiver 13 and the exhaust gas stream 15. The windows 19, 20 are cleaned by spraying the solvent, 28 onto the windows 19, 20 while wiping them to remove particulate matter 14; the sprayer 31 intermittently operable and the wiper arms 22 continuously operable for a first predetermined time period, preferably lasting about twenty seconds. The cleaning action is then interrupted and an accurate opacity monitor reading is obtained during a second predetermined time period by directing the light beam 34 across the exhaust stack 16 from the transmitter 10 via the first window 19, through the exhaust gas stream 15 to the receiver via the second window 20. The second time period preferably lasts about ten seconds. By alternately repeating the step of continually cleaning the windows 19, 20 by intermittently spraying a volatile nonflammable cleaning solvent 28 onto each of the windows 19, 20 while wiping the solvent 28 and particulate matter 14 therefrom during the first predetermined time period, with the step of obtaining an accurate opacity monitor reading during the second predetermined time period, a larger percentage of valid opacity monitor readings can be obtained within the regulatory-defined rate of once every thirty seconds.

Figure 4:
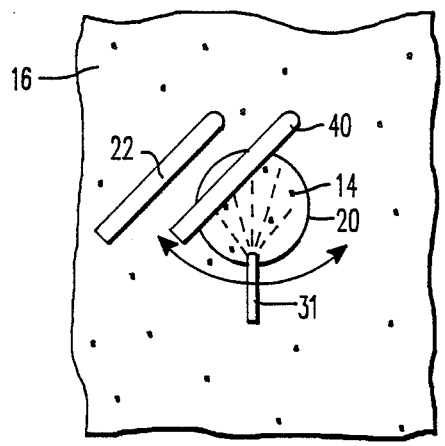
FIG. 4 is a view taken along the line IV—IV of FIG. 3 showing a second embodiment of the invention.

A second method of obtaining accurate opacity monitor readings would incorporate a reciprocating brush 40 along with the reciprocating resilient wiper arm 22 to continually clean the windows 19, 20. Since the exhaust stack 16 defines a relatively dry environment, it may not be necessary to spray the cleaning solvent 28 onto the windows 19, 20 during the first predetermined time period to effectively keep them free of particulate matter 14. Hence a second embodiment (FIG. 4) of a method and apparatus to periodically obtain accurate opacity monitor readings from a shielded monitor associated with an exhaust stack 16 would be as follows: A reciprocating brush 40 (or other means such as a conventional air blower) operably associated with each window 19, 20 is first used to minimize accumulation of particulate matter 14 on a surface of the windows 19, 20 facing the exhaust gas stream 15 during a first predetermined time period, this step preferably lasting about fifteen seconds. Then the step of intermittently spraying a volatile nonflammable cleaning solvent 28 onto each of the windows 19, 20 while completely wiping the solvent 28 and particulate matter 14 from the windows 19, 20 with a reciprocating wiper arm 22 in resilient engagement with each of the windows 19, 20 would be performed during a second predetermined time period, preferably lasting about ten seconds. Then an accurate opacity monitor reading would be obtained during a third predetermined time period, preferably lasting about five seconds. These steps are then sequentially repeated in order to periodically obtain an accurate opacity monitor reading every thirty seconds.

It is to be understood that while an opacity monitor reading is being obtained, the wiper arm 22 and/or brush 40 are stopped at a point along its reciprocating movement such that the arm 22 and/or brush 40 do not interfere with the light beam 34 being transmitted or received through the windows 19, 20, respectively. Also, use of the term "accurate" is meant to refer to an opacity monitor reading which is unaffected by the heretofore accumulation of particulate matter on an unshielded monitor which is in direct communication with an exhaust gas stream.

Since an exhaust stack 16 defines a relatively harsh environment—temperatures of the exhaust gas stream 15 generally range around 93° C. (200° F.), and may be slightly acidic depending upon the age of the plant and make-up of material being burned—the wiper arm 22 and brush 40 should be made of a material which can withstand such conditions. When needed, the wiper 22 and brush 40 can be periodically replaced during one of the required calibration checks. Also, the wiper 22 should preferably clean the entire surface of the windows or lenses 19, 20 since the light beam 34 may fall anywhere thereon due to vibrational effects. A typical light beam 34, continuously sent from the transmitter 10, has a diameter of about 6.35 mm (0.25") which will expand before reaching the receiver 13 on the opposite side of the stack 16. Due to this natural widening of the beam 34 and the vibrational effects, the windows 19, 20 should be made of sufficient size in order to allow the entire beam 34 to pass through the windows 19, 20. Generally, the lens of a typical monitor is about 50.8 mm (2") in diameter; hence the protective windows 19, 20 should be approximately the same size or larger. Therefore, a typical wiper arm 22 or brush 40 would be somewhat larger than the diameter to insure that the entire surfaces of the windows 19, 20 are clean, since the light beam may be sent or received at any point on the surface.

To minimize scratching of the windows 19, 20, they would be made of an extremely hard and scratch-resistant material, such as sapphire or silica. Scratching of the windows 19, 20 is to be avoided since a scratch would affect transmissibility of the light beam 34 through the windows 19, 20 and give rise to a false opacity reading as well. Also a material having an extreme hardness quality would have a longer life within the relatively harsh environment of an exhaust stack 16. Sapphire is also quite chemically resistant and thermal shock resistant, which are properties quite desirable for this type of environment; materials having similar properties could also be utilized.

DESCRIPTION OF A SECOND EMBODIMENT

As an alternative embodiment, the device itself may operate intermittently, based on need (as represented by loss in transmission). The period of cleaning under normal conditions can be performed on the order of once every 15 to 30 minutes, the specified interval being based upon the amount of contamination, or particulate matter 14, present in the exhaust gas stream 15. Also, during the period in time when cleaning is not being performed, the brush 40 may be used, preferably about every 30 seconds, to wipe windows 19, 20 clear of particulate matter 14. The steps of spraying a cleaning solvent 28 onto the windows and then wiping with the wiper arm 22, can then be performed periodically, such as every thirty minutes. In this manner less matter, in the form of cleaning solvent, is introduced into the exhaust gas stream 15. Thus the windows need only be cleaned during the specified interval as often as the transmission of valid opacity monitor data is required (e.g., when transmission and reception of the light beam 34 is less than the regulatory defined 90%).

With an opacity monitor that is continually kept clean with a cleaning device disposed adjacent to the monitor within the stack, the daily maintenance checks now required could be reduced significantly (less than half). It would not be necessary to remove or disassemble the monitor every day for cleaning. Also, since less of this routine maintenance is required, the monitor need be disassembled and checked less often, on the order of every other day, for things such as alignment of the light beam or other internal electrical checks that currently must be made when the monitor is disassembled or "opened up" for cleaning. In this manner, fossil fuel fired power plant operators can increase the percentage of valid data obtained to substantially reduce the possibility of having to pay regulatory fines.

While specific embodiments of the invention have been described in detail, it will be appreciated by those skilled in the art that various modifications and alterations would be developed in light of the overall teachings of the disclosure. Accordingly, the particular arrangements disclosed are meant to be illustrative only and not limiting as to the scope of the invention which is to be given the full breadth of the appended claims and in any and all equivalents thereof.

What is claimed is:

1. In an opacity monitor associated with an exhaust stack, said monitor having a transmitter and a receiver which cooperate to measure a quantity of particulate matter in an exhaust gas stream, a method of periodically obtaining opacity monitor readings comprising the steps of:
   (a) shielding the monitor from the exhaust gas stream by placing two windows adjacent to the monitor, a first window being placed between said transmitter and said exhaust gas stream and a second window being placed between said receiver and said exhaust gas stream;
   (b) cleaning at least one of said windows for a first predetermined time period by spraying a volatile nonflammable cleaning solvent onto said window by means of a sprayer intermittently operable during the first predetermined time period while wiping said window with a reciprocating wiper arm in resilient engagement therewith, said wiper arm continuously operable during the first predetermined time period;
   (c) then obtaining an opacity monitor reading by directing a light beam across the exhaust stack from the transmitter via the first window through the exhaust gas stream to the receiver via the second window during a second predetermined time period; and
   (d) alternately repeating the step of cleaning said window for the first predetermined time period with the step of obtaining an opacity monitor reading during the second predetermined time period.

2. The method as recited in claim 1, wherein the first predetermined period and the second predetermined period total thirty seconds, such that an opacity monitor reading is periodically obtained every thirty seconds.

3. The method as recited in claim 2, wherein the first predetermined time period is about twenty seconds, and the second predetermined time period is about ten seconds.

4. The method as recited in claim 1, wherein the step of shielding the monitor from the exhaust gas stream consists of placing two windows made of sapphire material between the transmitter and receiver and the exhaust gas stream.

5. The method as recited in claim 1, wherein the step of intermittently spraying a volatile nonflammable cleaning solvent onto each of said windows during the first predetermined time period consists of spraying 1,1,1 trichloroethane onto each of said windows.

6. The method as recited in claim 1, wherein the step of intermittently spraying a volatile nonflammable cleaning solvent onto each of said windows during the first predetermined time period consists of spraying water onto each of said windows.

7. In an opacity monitor associated with an exhaust stack said monitor having a transmitter and a receiver which cooperate to measure a quantity of particulate matter in an exhaust gas stream, a method of periodically obtaining an opacity monitor reading every thirty seconds, said method comprising the steps of:
   (a) shielding the monitor from the exhaust gas stream by placing two windows made of scratch-resistant material adjacent to the monitor, a first window being placed between said transmitter and said exhaust gas stream and a second window being placed between said receiver and said exhaust gas stream, each of said windows having a surface facing said exhaust gas stream;

(b) brushing said surfaces of each of said windows with a reciprocating brush operably associated with each of said windows to minimize accumulation of particulate matter thereon, said brushing action being performed for a first predetermined time period;

(c) then cleaning said surfaces by spraying a volatile nonflammable cleaning solvent onto each of said surfaces while wiping the solvent and particulate matter from said surfaces of said windows with reciprocating wiper arms in resilient engagement with each of said surfaces, said spraying and wiping action being performed for a second predetermined time period;

(d) then obtaining an opacity monitor reading by directing a light beam across the exhaust stack from said transmitter via the first window through said exhaust gas stream, to be received by said receiver via the second window, said reading being obtained during a third predetermined time period; and (e) sequentially repeating the steps of: brushing said surfaces of said windows for the first predetermined time period; and then cleaning said surfaces of said windows for the second predetermined time period; and then obtaining an opacity monitor reading during the third predetermined time period.

8. The method as recited in claim 7, wherein the first predetermined time period is about fifteen seconds, the second predetermined time period is about ten seconds, and the third predetermined time period is about five seconds.

9. The method as recited in claim 7, wherein the step of shielding the monitor from the exhaust gas stream consists of placing two windows made of sapphire material between the transmitter and receiver and the exhaust gas stream.

10. The method as recited in claim 7, wherein the step of cleaning said surfaces of said windows consists of intermittently spraying 1,1,1 trichloroethane onto each of said surfaces while wiping said surfaces of said windows.

11. The method as recited in claim 7, wherein the step of cleaning said surfaces of said windows consists of intermittently spraying water onto each of said surfaces while wiping said surfaces of said windows.

12. In an opacity monitor associated with an exhaust stack said monitor having a transmitter and a receiver which cooperate to measure a quantity of particulate matter in an exhaust gas stream by means of a light beam transmitted from the transmitter to the receiver, a method of cleaning an opacity monitor comprising the steps of:

(a) shielding the monitor from the exhaust gas stream by placing two windows made of scratch-resistant material adjacent to the monitor, a first window being placed between said transmitter and said exhaust gas stream and a second window being placed between said receiver and said exhaust gas stream, each of said windows having a surface facing said exhaust gas stream;

(b) brushing said surfaces of each of said windows with a reciprocating brush operably associated with each of said windows to minimize accumulation of particulate matter thereon, said brushing action being performed once every thirty seconds; and (c) then cleaning said surfaces by spraying a volatile nonflammable cleaning solvent onto each of said surfaces while wiping the solvent and particulate matter from said surfaces of said windows with reciprocating wiper arms in resilient engagement with each of said surfaces, said spraying and wiping action being performed at a specified interval.

13. The method as recited in claim 12, wherein the specific interval occurs when the transmission of the light beam is below 90%.

14. The method as recited in claim 12, wherein the specified interval is once every thirty minutes.

15. The method as recited in claim 12, wherein the step of shielding the monitor from the exhaust gas stream consists of placing two windows made of sapphire material between the transmitter and receiver and the exhaust gas stream.

16. The method as recited in claim 12, wherein the step of cleaning said surfaces of said windows consists of intermittently spraying water onto each of said surfaces while wiping said surfaces of said windows.

17. The method as recited in claim 12, wherein the step of cleaning said surfaces of said windows consists of intermittently spraying 1,1,1 trichloroethane onto each of said surfaces while wiping said surfaces of said windows.

* * * * *